United States Patent [19]

Witherby

[11] Patent Number: 5,028,233
[45] Date of Patent: Jul. 2, 1991

[54] DISPOSABLE PROPHY ANGLE

[75] Inventor: Kenneth Witherby, Broomfield, Colo.

[73] Assignee: Teledyne Industries, Inc., Los Angeles, Calif.

[21] Appl. No.: 439,414

[22] Filed: Nov. 21, 1989

[51] Int. Cl.[5] .............................................. A61C 3/06
[52] U.S. Cl. .................................... 433/125; 433/114
[58] Field of Search ............... 433/125, 126, 127, 114, 433/112

[56] References Cited

U.S. PATENT DOCUMENTS

| | | | |
|---|---|---|---|
| 3,163,934 | 1/1965 | Wiseman | 433/125 |
| 3,740,853 | 6/1973 | Brahler | 433/112 |
| 3,798,777 | 3/1974 | Reiter | 433/112 |
| 3,869,877 | 3/1975 | Brahler | 433/125 |
| 4,182,041 | 1/1980 | Girard | 433/126 |

FOREIGN PATENT DOCUMENTS

| | | | |
|---|---|---|---|
| 508696 | 10/1929 | Fed. Rep. of Germany | 433/126 |
| 876737 | 4/1953 | Fed. Rep. of Germany | 433/126 |

Primary Examiner—John G. Weiss
Assistant Examiner—Michael Lynch
Attorney, Agent, or Firm—Lockwood, Alex, FitzGibbon & Cummings

[57] ABSTRACT

A disposable prophy angle is permanently assembled from four plastic components each of which is integrally formed in one piece. Two of the components are mating half sections which when bonded together along a longitudinal mating plane form a housing for an input gear member secured in driving engagement with an output gear. The input gear with its rearwardly extending drive spindle is housed in an elongated tubular portion of the completed housing while the output gear, except for its protruding prophy cup-receiving mandrel or button, is housed in the nose portion on the front end. The housing has internal formations which provide thrust and support bearing elements for cooperating bearing elements on the gear members. The components can be mass-produced and assembled at low cost making it economic to discard the prophy angles after one use.

3 Claims, 1 Drawing Sheet

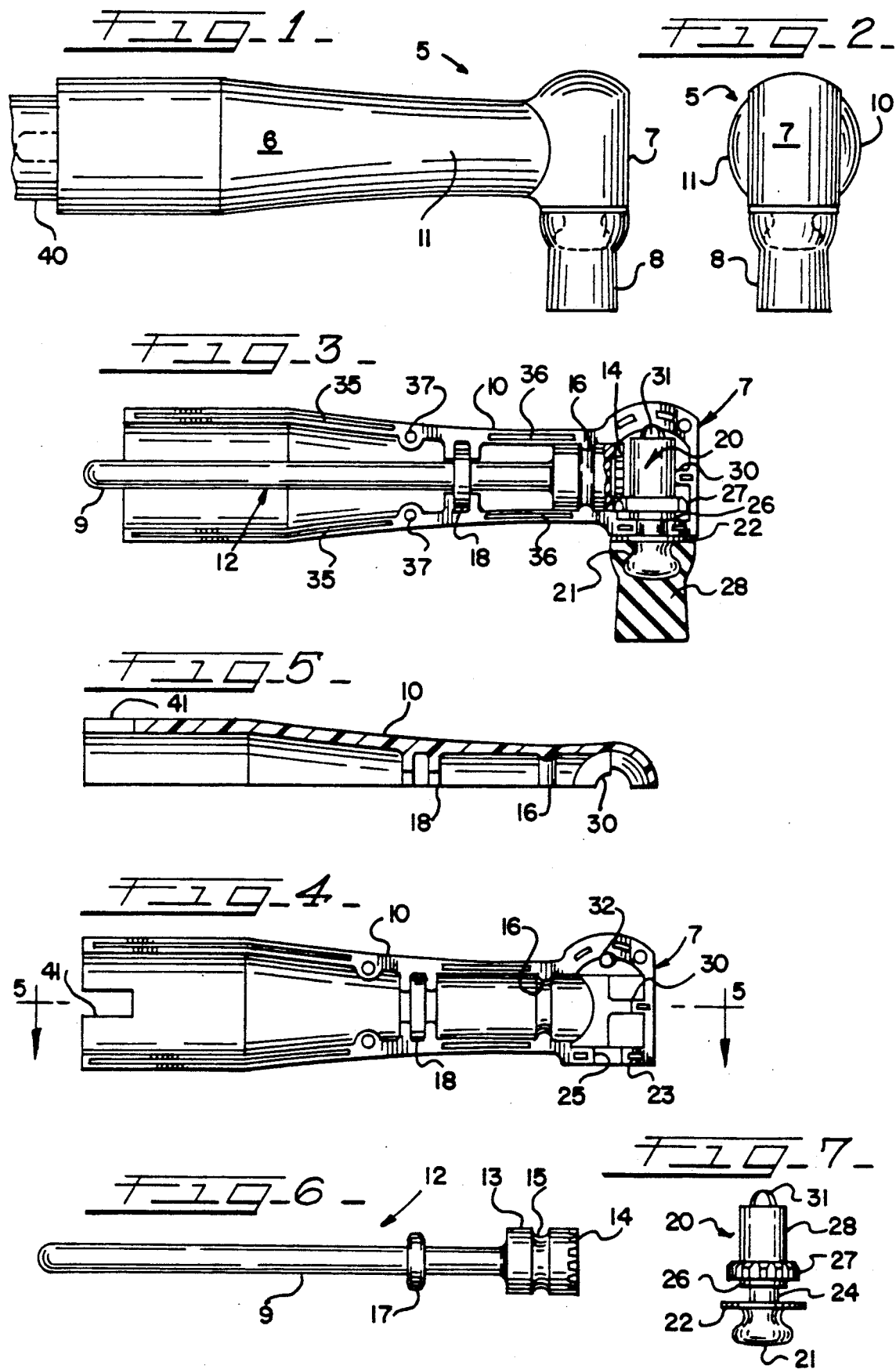

DISPOSABLE PROPHY ANGLE

This invention relates, generally, to improvements in disposable prophy angles adapted to be used on standard dental drive sheath and lock collets. More particularly, it relates to disposable (i.e. discardable after one use) prophy angles consisting of and assembled from four component members economically mass-produced from suitable plastics and readily assemblable into permanently assembled units.

Heretofore, two general types of prophy angles (i.e. dental prophylaxis right angle hand pieces) have been available. One type has been the relatively expensive permanent type formed of metal parts suitable for repeated usage and requiring sterilization. The other general type of prophy angle is the disposable type formed of plastics and which are disposable after one time use.

The object of the present invention, generally stated, is the provision of improved disposable prophy angles formed of only four components (not counting the prophy cup) with each component being integrally formed of plastic and which are readily assemblable on a production basis into permanently assembled units which are inexpensive, reliable, rugged and durable for one time use, and energy efficient in transmitting and delivering power from the input side to the output side so as to drive the prophy cups.

Certain other objects of the invention will be apparent to those skilled in the art in light of the following detailed description of a preferred embodiment of the invention taken in connection with the accompanying drawings, wherein:

FIG. 1 is a side elevational view of a disposable prophy angle embodying the present invention;

FIG. 2 is a right end elevational view of the prophy angle shown in FIG. 1;

FIG. 3 is a side elevational view of the prophy angle of FIG. 1 with one-half section of its housing having been removed and showing the remaining half section in side elevation and the input and output gear members in side elevation with the prophy cup shown in vertical section;

FIG. 4 is a elevational view of the housing half section shown in FIG. 3 with the working parts removed;

FIG. 5 is a sectional view taken on line 5—5 of FIG. 4;

FIG. 6 is a side view of the input gear forming part of the assembly shown in FIG. 3; and FIG. 7 is a side elevational view of the output gear forming the remaining part of component of the assembly shown in FIG. 3.

In FIGS. 1-3, the prophy angle is indicated generally at 5 having an elongated tubular portion 6 and a nose portion 7.

The prophy angle 5 is permanently assembled from four component members. A conventional prophy cup 8 being attached after the assembly is completed.

Two of the components members are mating left hand and right hand housing-forming members, one of which is indicated at 10 in FIGS. 2-5 and the other of which is indicated at 11 in FIGS. 1 and 2. It will be understood that except for being left handed and right handed the housing half sections 10 and 11 are identical being mirror images of each other.

The input gear is indicated generally at 12 in FIGS. 3 and 6. It has a cylindrical formation 13 at its inner or front end from the rear side of which a drive spindle or stem 9 extends. The cylindrical formation 13 has a face gear 14 formed on its front end. In its mid-portion the cylindrical formation 13 has an arcuate circumferential groove 15 which serves as rotary bearing element which is received and journaled in the circumferential stationary bearing ring 16 integrally formed on the interior of the housing half sections 10 and 11.

Spaced to the rear of the cylindrical end 13, the drive spindle or stem 9 has a integrally formed rotary thrust bearing element 17 which rotates in the stationary circumferential thrust bearing ring 18 formed by the mating together of the half sections 10 and 11.

The output gear component is indicated generally at 20 in FIGS. 3 and 7 being integrally formed in one piece. At its bottom end, the output gear member 20 has a mandrel or button formation 21 of conventional shape to receive and removably retain a conventional prophy cup 8. At the upper end of the button 21 there is a slinger ring or disk 22 the upper side of which rotates against the annular bottom surface 23 of the nose 7. Above the slinger ring 22 output gear 20 has a cylindrical rotary bearing element 24 which is journaled and rotates in the circular bearing 25 formed at the bottom of the nose 7. A shoulder 26 rotates on the top surface of the bearing 25 with a spur gear 27 being formed immediately above the shoulder 26. As will be seen from FIG. 3, the teeth of the spur gear 27 intermesh with the teeth on the face gear 14 so as to have driving relationship therewith.

On the output gear 20 above the gear 27 is a cylindrical rotary bearing 28 which rotates in engagement with a semi-circular bearing 30 formed in the front sidewall of the nose 7. At its upper end, the output gear element 20 has a hemi-spherical thrust bearing 31 which rotates in bearing socket 32 formed in the cap portion of the nose 7.

The four component members of the prophy angle 5 may be formed from suitable plastic materials which have adequate strength and durability for their respective intended functions. By way of example only, the housing half sections 10 and 11 may be formed from a suitable grade of nylon (e.g. Nylon 6). The input gear member 12 and the output gear member 20 may be formed from nylon or acetal resin (e.g. Nylon 6/6-10% glass filled or Acetal resin - 10% glass filled). These plastics are sufficiently inexpensive and are economically producable in production quantities.

In assembly, the input gear member 12 and output gear member 20 are inserted into one of the opened half sections (e.g. section 10) of the housing and then the remaining housing half section is placed on this preliminary assembly and then the housing half sections are securely bonded together such as by sonic welding using known techniques and equipment. The sonic welding operation is facilitated by using energy directors 35 and 36 and pins 37—37.

In use, the disposable prophy 5 is mounted in conventional manner onto a standard dental drive sheath and lock collet as indicated at 40 in FIG. 1. The housing half sections 10 and 11 are formed with slots 41—41 to facilitate the connection. The input drive gear member 12 is driven as called upon by the operator and the output gear member 20 is driven in turn so as to rotate the prophy cup 21 at the desired speed within the range available.

As will be apparent from FIG. 3, there is a right angle drive relationship between the face gear 14 and the spur gear 27 with separating loads being normal to the gear teeth. It will be seen that the separating loads on the face gear 14 are absorbed by the bearings 15-16 and 17-18. The separating loads on the spur gear 27 are absorbed by the bearing elements 20-30 and 31-32.

The interengaging arcuate surfaces of the circumferential groove 15 and the spherical ring 16 serve to both retain the input gear element 14 in place while allowing for an adequate degree of misalignment when the drive spindle or stem is engaged and driven by the drive collet of the dental drive sheath and lock collet, thus preventing induced stresses caused by preloading of the components of the operating cycle.

What is claimed is:

1. A disposable prophy angle permanently assembled from four plastic component members consisting of a horizontally oriented integral input gear member; a vertically oriented integral output gear member; and a pair of mating integral body forming members bonded together on a common longitudinal plane after insertion therebetween of said gear members;

said input gear member having a cylindrical formation at its inner end with a driving face gear on its vertical front surface, a rearwardly extending drive spindle, and a rotary thrust bearing element on said drive spindle;

said output gear member having a protruding prophy cup-receiving button on its bottom end, a laterally extending slinger ring above said button, a lower rotary bearing element above said slinger ring, a driven gear above said rotary bearing element, an upper rotary bearing element above said driven gear, and a rotary cap bearing element on its upper end; and said bonded together body forming members providing a housing for said gear members including a laterally extending tubular portion which houses said input gear member and a vertically oriented nose portion which houses said output gear member; said laterally extending tubular portion having a stationary thrust bearing element in which said rotary thrust bearing element rotates and which together therewith absorbs axial thrusts on said drive spindle and a stationary bearing formation in which said cylindrical face gear formation is journaled; said nose portion having an annular bottom surface against which said slinger ring rotates, a stationary bearing element in which said lower rotary bearing element is journaled, a partial stationary bearing element against which said upper rotary bearing element rotates and which absorbs forward thrusts on said output gear member, and a stationary bearing socket in the cap of said nose portion in which rotary cap bearing element rotates;

said face gear and said driven gear being intermeshed whereby rotation of said drive spindle produces rotation of said protruding prophy cup-receiving button.

2. The disposable prophy angle called for in claim 1 wherein said body-forming members are made of nylon and said gear members are formed of glass filled nylon or acetal resin.

3. A disposable prophy angle permanently assembled from four plastic component members consisting of a horizontally oriented integral input gear member; a vertically oriented integral output gear member; and a pair of mating integral body forming members bonded together on a common longitudinal plane after insertion therebetween of said gear members;

said input gear member having a cylindrical formation at its inner end with a driving face gear on its vertical front surface, a rearwardly extending drive spindle, and a rotary thrust bearing flange on said drive spindle spaced rearwardly from said cylindrical formation;

said output gear member having a protruding prophy cup-receiving button on its bottom end, a laterally extending slinger ring above said button, a lower rotary bearing element above said slinger ring, a driven gear above said rotary bearing element, an upper cylindrical rotary bearing element above said driven gear, and a hemi-spherical rotary cap bearing element on its upper end; and said bonded together body forming members providing a housing for said gear members including a laterally extending tubular portion which houses said input gear member and a vertically oriented nose portion which houses said output gear member; said laterally extending tubular portion having a grooved stationary thrust bearing element in which said rotary thrust bearing flange rotates and which together therewith absorbs axial thrusts on said drive spindle and a stationary bearing formation in which said cylindrical face gear formation is journaled; said nose portion having annular bottom surface against which said slinger ring rotates, a stationary bearing element in which said lower rotary bearing element is journaled, a semi-cylindrical stationary bearing flange against which said upper cylindrical rotary bearing element rotates and which absorbs forwards thrust on said output gear member, and a stationary bearing socket in the cap of said nose portion in which rotary cap bearing element matingly rotates;

said face gear and said driven gear being intermeshed whereby rotation of said drive spindle produces rotation of said protruding prophy cup-receiving button.

* * * * *